United States Patent
Shanbrom

(10) Patent No.: US 7,411,006 B2
(45) Date of Patent: *Aug. 12, 2008

(54) ENHANCED PRODUCTION OF BLOOD CLOTTING FACTORS AND FIBRIN FABRIC

(75) Inventor: Edward Shanbrom, Santa Ana, CA (US)

(73) Assignee: Shanbrom Technologies, LLC, Ojai, CA (US)

( * ) Notice: Subject to any disclaimer, the term of this patent is extended or adjusted under 35 U.S.C. 154(b) by 399 days.

This patent is subject to a terminal disclaimer.

(21) Appl. No.: 10/459,804

(22) Filed: Jun. 12, 2003

(65) Prior Publication Data

US 2005/0196393 A1  Sep. 8, 2005

Related U.S. Application Data

(63) Continuation-in-part of application No. 10/280,501, filed on Oct. 25, 2002, now Pat. No. 7,297,716, which is a continuation-in-part of application No. PCT/US02/03996, filed on Feb. 7, 2002, and a continuation-in-part of application No. 09/778,681, filed on Feb. 7, 2001, now Pat. No. 6,541,518, which is a continuation-in-part of application No. 09/694,178, filed on Oct. 23, 2000, now Pat. No. 6,881,731.

(60) Provisional application No. 60/278,496, filed on Mar. 23, 2001.

(51) Int. Cl.
*A61K 47/00* (2006.01)
*A01N 25/00* (2006.01)
(52) U.S. Cl. ....................... 514/784; 514/785
(58) Field of Classification Search ........ 424/667; 514/784, 785
See application file for complete search history.

(56) References Cited

U.S. PATENT DOCUMENTS 5,981,254 A * 11/1999 Bui-Khac ............ 435/214

* cited by examiner

*Primary Examiner*—Alton Pryor
(74) *Attorney, Agent, or Firm*—Venable LLP; Stefan J. Kirchanski

(57) ABSTRACT

The blood collection, processing and transfer by separation of discrete components containing additional citrate (at least about trisodium citrate 9% w/v) in one or other of collection or processing bag provides for enhanced yield and purity of cryoprecipitate. Inhibiting the activation or denaturation of blood components including blood cells and plasma proteins and with the removal of the activated and denatured components thereby improving safety and efficacy of end products. The inventive process is particularly suited to an improved extraction process to yield concentrated clotting factors from single donors or limited pools without use of chromatography. Following extraction the remaining cryoprecipitate can advantageously be formed into a fibrin fabric used in surgeries and in the treatment of wounds.

17 Claims, 1 Drawing Sheet

ENHANCED PRODUCTION OF BLOOD
CLOTTING FACTORS AND FIBRIN FABRIC

RELATED APPLICATIONS

The present application is a continuation-in-part of and claims priority from U.S. patent application Ser. No. 10/280,501, filed Oct. 25, 2002 now U.S. Pat. No. 7,297,716, which in turn was a continuation-in-part of International Patent Application No. PCT/US02/03996 filed on Feb. 7, 2002, designating the United States, which in turn was continuation-in-part of U.S. patent application Ser. No. 09/694,178 filed Oct. 23, 2000 now U.S. Pat. No. 6,881,731, and U.S. patent application Ser. No. 09/778,681 filed on 7 Feb. 2001 now U.S. Pat. No. 6,541,518 and U.S. patent application Ser. No. 60/278,496 filed 23 Mar. 2001. To the extent allowable, all these applications are incorporated by reference herein.

BACKGROUND OF THE INVENTION

1. Area of the Art

The present invention relates to the art of producing coagulation factor concentrates from blood plasma.

The invention is directed to enhancing the yield and purity of fractionated plasma proteins.

2. Description of the Prior Art

There are a number of medical indications for administration of "clotting" or "coagulation" factors from human blood. These factors are proteins that cause the clotting of blood to staunch bleeding from wounds, etc. Individuals with any of a series of genetic abnormalities affecting the proteins responsible for blood coagulation are afflicted with a disease (hemophilia) in which the blood fails to clot normally, subjecting the individual to the danger of uncontrolled bleeding. For many years, this condition has been treated by administering concentrates of the missing or defective proteins. Many clotting factors are synthesized in the liver so that victims of liver disease are also in need of augmentation of their clotting factors. Additionally, there are other important medical uses for clotting-related factors including the use of fibrin to produce "fibrin sealant" or "fibrin glue" or "fibrin fabric".

While some of the clotting factors are currently produced through biotechnology, at this time there is still no cost effective method of artificially manufacturing all of these proteins or these proteins in sufficient quantities. Further, the "artificially produced" factors made by recombinant and related technologies tend to be more expensive. Many of the "minor" factors are not yet (and may never be) available from biotechnology sources and so must be purified from donated human blood. Also, there is often a synergy between factors whereby a single administered recombinant factor is not nearly as effective as a natural mixed fraction produced from fractionated blood.

There is also a special problem in Third World countries where the biotechnology products are generally either not available or not affordable. Therefore, much of the supply of anti-hemophilia factor (AHF, also known as Factor VIII), and other blood clotting factors are prepared from pooled human plasma. A hemophiliac requires treatment for a whole lifetime. Victims of liver disease and other users of clotting factors may also require prolonged treatment. Therefore, these patients are exposed to blood products produced from the blood of a large number of donors.

The presence of AIDS (Acquired Immuno Deficiency Syndrome) virus or HIV in the blood supply means that hemophiliacs and other users of clotting factors have become infected with this terrible disease. Although tests to screen out AIDS-tainted blood have been improved, some infected blood does slip by. Even if the AIDS problem is solved, the danger of other blood-borne diseases, such as the various types of hepatitis and other, as yet unknown, infectious agents, makes it desirable to reduce or eliminate virus and other disease organisms from plasma used to prepare clotting factors. One way of achieving this goal is to replace pooled plasma products with products from a single donor (or pooled from a limited number of donors) since with pooled products "one bad apple spoils the entire barrel", and the larger the number of donors in a pool, the greater the chance of "spoilage".

Even with the use of clotting factors derived from a single donor, there is still danger. Even though tests may show the donor is free of known disease, the donor may be incubating a disease that will later show up on the tests, or the donor may harbor a yet unknown disease or a yet unknown strain of a known disease. These dangers have been lessened by use of plasma pre-treatments that inactivate disease organisms. Unfortunately, the best commonly used treatments either do not inactivate all types of disease organisms or damage the labile clotting factors during the process of inactivating disease organisms.

The basic methods for preparing clotting factor concentrates from blood have not changed greatly over the last few decades. Generally, a concentrate of clotting factors is derived from pooled plasma by a cryoprecipitation step. The plasma is frozen and then thawed. During the freezing process certain proteins precipitate to form a "cryoprecipitate." Various additives such as ethanol and/or polyethylene glycol are often added to enhance the efficiency of the cryoprecipitation step. Following cryoprecipitation, the partially purified factors may be further purified by additional precipitation steps or by chromatographic methods, and most recently by methods using monoclonal antibodies. For additional information on the basic techniques of clotting factor purification and the history of the development of these methods, the reader is directed to U.S. Pat. Nos. 3,560,475, 3,631,018, 3,682,881, 4,069,216, and 4,305,871 and 5,770,704 by the present inventor, the contents of which are incorporated herein by reference, and the references cited therein. Because these and similar methods usually involve pools of plasma from many donors, the relative safety of a single or limited donor pool is generally not attained.

After the cryoprecipitate has been removed, the supernatant remaining is usually subjected to further purification by means of ethanol precipitation to yield gamma globulin (immune globulin) and albumin, both of which have significant uses in medicine. After the clotting factors have been purified from the cryoprecipitate, the leftover fibrinogen (including fibronectin and some other factors) is either discarded or used to produce some type of fibrin sealant or bandage.

SUMMARY OF THE INVENTION

It is an object of the present invention to enhance the yield and purity of cryoprecipitate;

It is an additional object of the present invention to provide an improved method for blood fractionation that enables use of limited donor pools;

It is a further object of the present invention to provide a simplified procedure for making relatively high purity clotting factor concentrate; and It is another object of the present invention to produce a "fibrin fabric" that can be used in surgery and to treat wounds.

Derivatives of simple carboxylic acids, particularly trisodium citrate and other citric acid salts (hereinafter "citrate")

are shown to be unexpectedly effective agents for enhancing the production of blood clotting factors. It is believed that other small carboxylic acids, isocitric acid in particular, show similar properties. However, to date most of the tests have been made with citric acid and its salts. Addition of citrate to plasma, especially at concentrations between 2 and 15% by weight, does not apparently damage labile proteins. However, in this concentration range citrate is effective in inactivating or inhibiting a variety of pathogenic microorganisms. Further, the added citrate potentiates or enhances the killing of microorganisms by heat treatment. That is, heating of the material to relatively low temperatures (i.e., usually above about 45° C.) which do not denature proteins nevertheless enhances the killing of microorganisms in the presence of citrate.

Most significantly, added citrate causes a dramatic increase in the weight of cryoprecipitate that can be produced from plasma by the usual procedures. The majority of the major clotting factors are greatly concentrated in the resulting cryoprecipitate—to the result that the supernatant contains little if any of these clotting factors. It is apparent that increasing the amount of citrate in blood bags so that the final concentration will be at least 2% (and preferably 10-15%) by weight results in plasma that can be used to produce enriched cryoprecipitate. The added citrate can also help eliminate or suppress contaminating microorganisms and can itself be removed later by ion exchange or similar methods well known in the art.

The added citrate enhances the yield and purity of cryoprecipitate. Not only does added citrate increase the amount of cryoprecipitate; it simplifies the process by eliminating the requirement for freezing. Furthermore, added citrate can inhibit the activation or denaturation of blood components such as plasma proteins and/or facilitate the removal of the activated or denatured components and improves the safety and efficacy of end products.

According to the invention there is provided a method for enhancing the purity and safety of multiple derivative components of blood including blood cells and plasma. In this method, there is the step of adding at least about 2%, and more preferably 10-15%, by weight of carboxylic acid salt or equivalent weight of carboxylic acid to the blood or plasma.

At least 2%, and more preferably 10-15% by weight of a salt of citric acid (or equivalent weight of citric acid with concomitant control of pH) is added to the plasma as soon as practicable after it is removed from the donor. The plasma may be collected into a blood bag containing the carboxylic acid or the carboxylic acid salt. This blood bag may be different from a bag or container used to collect whole blood. Alternatively or additionally, an amount of additional carboxylic acid or the salt thereof may be added directly to the bag used to collect the whole blood.

In a further preferred form of the invention, citrate is used appropriately in the collection of blood, in the processing and transfer of blood and in a separation of discrete blood components. Citrate is used in increased quantities, preferably 10-15% weight by volume, over the level traditionally employed for anticoagulation in one or other collection or processing bag.

Once the enriched cryoprecipitate is produced according to the inventive method highly purified Factor VIII can be extracted from that cryoprecipitate. The cryoprecipitate is extracted with cold (below about 10° C.) saline (0.9% wt/vol), containing about 0.3M calcium chloride to yield a clotting factor concentrate. Compared to extraction with saline or water, this procedure dissolves less of the fibrinogen and other proteins found in the cryoprecipitate. Therefore, this improved extraction can be used on plasma from a single donor or from a limited donor pool to make a useable clotting factor concentrate under blood bank conditions.

After the clotting factors have been extracted, the remaining insoluble fibrinogen can be converted in to a fibrin fabric. If the extracted cryoprecipitate is heated to about 50° C., it form a gel which can readily be formed into slabs which will harden further over 8-12 hr to form a tough membrane or fabric which can then be used to dress wounds. This dressing material will gradually be broken down and absorbed by the body.

DETAILED DESCRIPTION OF THE INVENTION

Figure 1:
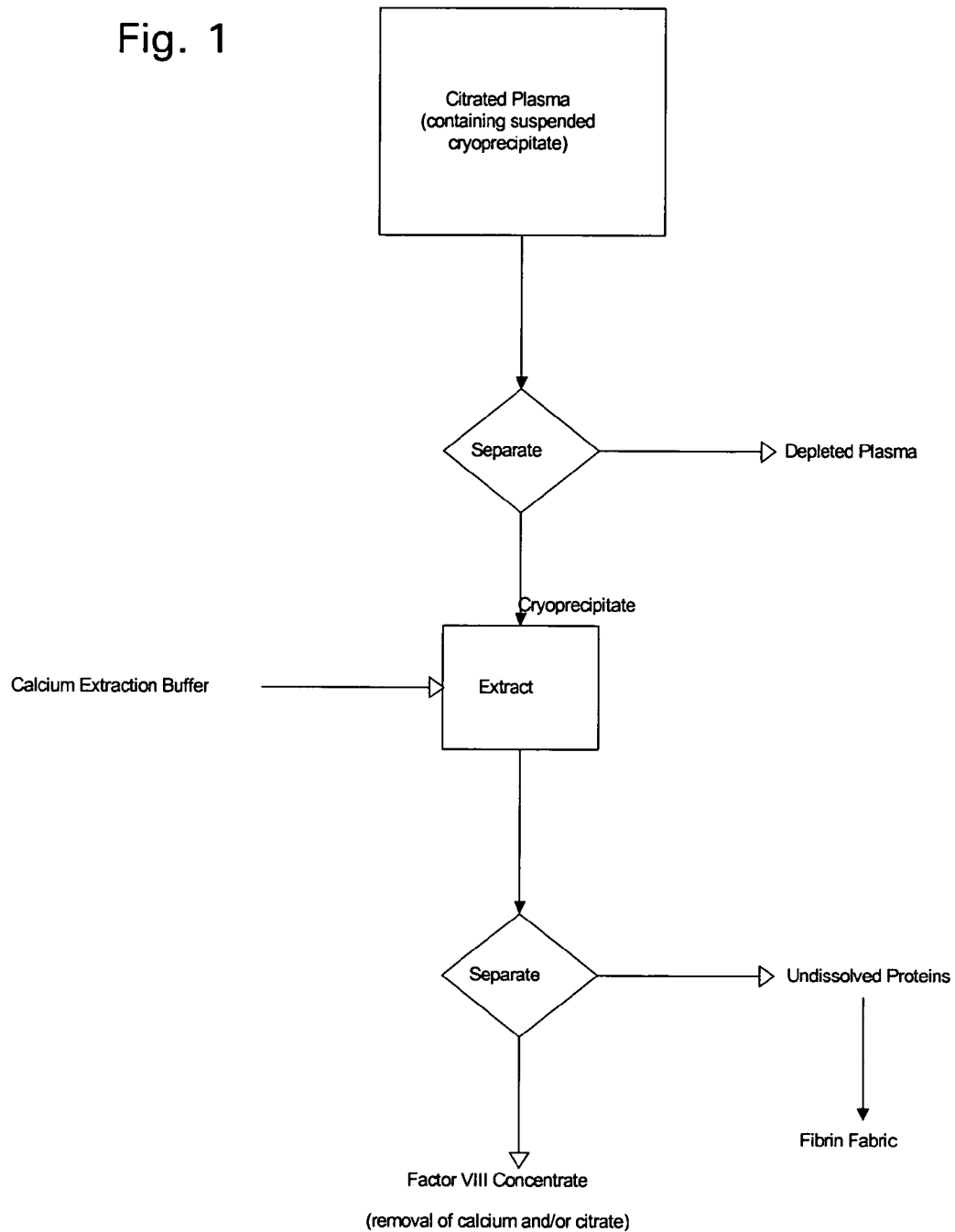
FIG. 1 is a flow diagram showing the extraction procedure of the present invention used to make a clotting factor concentrate and fibrin fabric.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a simple procedure for enhanced production of Factor VIII from collected plasma.

The traditional method for producing clotting factors, as well as many of the presently used methods, operate because many of the plasma proteins responsible for blood clotting precipitate (i.e., form cryoprecipitate) from solution at low temperatures. When a protein solution is frozen, ice crystals form and protein molecules, which are excluded from the crystals become increasingly concentrated. Cooling or freezing the water also lowers the chemical activity of the water. Depending on the particular proteins, the proteins may actually fall out of solution, i.e., form a precipitate, if the protein more readily interacts with itself or with other proteins than with water. When the chemical activity of water is lowered such precipitation is favored.

Such precipitation may denature the proteins (make them irreversibly insoluble), so it is usual to freeze protein solutions rapidly and to a low temperature (i.e., −20° C. or lower) to minimize the formation of ice crystals and to prevent the growth of those crystals that do form. This is done to limit protein denaturation on ice crystal surfaces. Blood coagulation enzymes are extremely sensitive. Even when freezing is carried out with great care, ice crystals may cause "activation" of the prothrombin complex, resulting in spontaneous clot formation and loss of coagulation factors to proteolysis and/or clot formation. It now appears that the most significant amount of such activation occurs during the thawing process as opposed to during the freezing process.

The first step in the typical procedure for producing plasma cryoprecipitate is to centrifuge whole blood to separate the plasma from the red blood cells. This procedure is well known in the art and is often accomplished in special centrifuges that hold individual blood bags so that the plasma/red cell separation occurs without even opening the blood bag. Following the centrifugation, it is common practice to express the supernatant plasma into a "satellite" blood bag for further processing. Once the plasma is separated from red and white blood cells, the typical procedure is to rapidly freeze the plasma and to then slowly thaw the frozen plasma at about 4° C., during which thawing the clotting factors and other proteins form a cryoprecipitate which can be readily harvested by filtration or centrifugation. This cryoprecipitate is not rendered irreversibly insoluble and can be readily redissolved in a saline buffer, or even water, as is well known in the art.

Cryoprecipitation is generally believed to result when the removal of water from the immediate vicinity of the protein molecules causes the protein molecules to preferentially associate with each other rather than with water. This "removal" of water may represent changes in the solubility of the proteins with changes in temperature (i.e., water becomes less effective at dissolving the proteins). The process may also be accomplished or enhanced by using additives which "tie up" the water and cause it to interact with the proteins to a lesser degree. These additive substances can be any of a number of hydrophilic materials such as ethanol, polyethylene glycol, heparin, Pluronic RTM polyol polymers and various "salts" such as ammonium sulfate or ammonium acetate.

The "salting out" of proteins from solution is a classical biochemical procedure. These and other materials used to increase the yield of cryoprecipitate generally operate to decrease the effective activity of water in the mixture. That is, the water molecules preferentially interact with the added hydrophilic material instead of with the proteins. This permits the proteins to interact with each other and, therefore, precipitate from solution. Similarly, lowering the temperature—especially to the freezing point—also decreases the activity of water, allowing protein-protein interactions to predominate.

The hydrophilic additives just mentioned have the advantage of being relatively inexpensive and easy to use. However, their use usually necessitates additional washing steps to ensure that the additives are not carried over into the final product. Some additives may also damage or denature the labile clotting factors one is seeking to purify. The present inventor has discovered that one of the agents frequently used as an anticoagulant in blood fractionation unexpectedly serves to enhance cryoprecipitate formation. Citrate (trisodium citrate or similar salts as well as derivatives of other low molecular weight carboxylic acids such as isocitric acid) has unusually favorable properties when used in blood fractionation procedures at levels significantly higher than those traditionally used as an anticoagulant. Citrate is a fairly effective chelator of calcium ions. By effectively lowering the calcium ion level, citrate inhibits a considerable variety of blood clotting pathways which depend on the presence of calcium ions. However, citrate has not been employed as an agent to simultaneously prevent loss through activation and to enhance the preparation of cryoprecipitate proteins from plasma.

The following table shows the enhanced production of cryoprecipitate caused by increasing the level of trisodium citrate in plasma. As the citrate is increased, the weight of recovered cryoprecipitate is increase. When the cryoprecipitate is redissolved in a fixed quantity of buffer or water, the increasing amount of cryoprecipitate yields increasing amounts of Factor VIII and fibrinogen as compared to the original plasma. It seems reasonable to speculate that since one action of citrate is to inhibit the activation of clotting factors, which act as proteases when activated, inhibition of activation prevents digestion of clotting proteins thus increasing the yield of these proteins. It is important to appreciate that the increased amounts of citrate are added to the plasma as soon as practicable—preferably before any freezing of the plasma. If the plasma is frozen without the added citrate, it is imperative that added citrate be present during the thawing process so that losses due to activation of clotting factors during thawing are prevented.

| Treatment | Cryoprecipitate | Factor VIII | Fibrinogen |
|---|---|---|---|
| control | 0.1 g | 120% | 46 mg/dl |
| 2% citrate | 0.3 g | 180% | 53 mg/dl |
| 5% citrate | 0.9 g | 247% | 105 mg/dl |
| 10% citrate | 3.0 g | 622% | 152 mg/dl |

These results indicate that as the citrate concentration is increased the amount of recovered clotting factors increases linearly. There is a further increase of cryoprecipitate with 15% citrate; however, at that concentration of citrate it appears that there is an increase in the precipitation of other proteins. The optimum concentration lies between about 10% and about 15% weight/volume citrate. Tests have shown that besides more than 95% of the Factor VIII and Fibrinogen, virtually all of the Fibronectin and the von Willdebrand's factor become concentrated in the citrate-enhanced cryoprecipitate.

Further insight into the citrate effect is gleaned by analyzing the distribution of citrate in a typical cryoprecipitate experiment. For this experiment, one unit (about 200 ml) of plasma was brought to 10% wt/vol. trisodium citrate. The citrate stock solution was adjusted to neutral pH with HCl or acetic acid prior to use, and in all experiments pH measurements showed that natural buffering of the plasma prevented significant changes in pH. This citrate-treated plasma was frozen and cryoprecipitate was collected in the usual manner. It important that the thawed material be gently mixed for sufficient time (12 hours) to permit maximal precipitation to occur. As an aside, in producing citrate cryoprecipitate it is preferred to add the citrate prior to freezing, but good results are achieved by adding the citrate during the thawing process (to the frozen plasma before thawing actually starts). As will be demonstrated below, actual freezing is not necessary.

The volume of cryoprecipitate formed from the unit of plasma was approximately 20 ml—that is, 10% of the total volume. Surprisingly, an analysis of the cryoprecipitate and the supernatant plasma showed that about 12 g (60%) of the citrate was concentrated in the cryoprecipitate with only 40% being left in the supernatant. This indicates that there is a strong interaction between the cryoprecipitate proteins and the citrate. The proteins become "citrified" or "citrated" upon incubation with elevated concentrations of citrate. Further, while normal cryoprecipitate can be redissolved in water or buffer, citrated cryoprecipitate is somewhat less soluble in water. It is soluble, however, in saline buffer and most soluble when the buffer contains citrate. One way of explaining these phenomena is to assume that the multiple negative charges on the citrate molecule are interacting with positive charges on the cryoprecipitate proteins to cross-link them. Added citrate "satisfies" these positive charges so that cross-linking is diminished. Because of the inclusion of clotting proteins in the cryoprecipitate, it is tempting to theorize that the clotting proteins share some sort of positive charge motif that interacts with the citrate molecules. It may be that other proteins will also become "citrified" if incubated with a sufficiently high concentration of citrate.

In summary, compared to "normal" cryoprecipitate citrated cryoprecipitate contains essentially all of the Fibrinogen, Fibronectin, Factor VIII and von Willdebrand's factor. The citrated cryoprecipitate may also contain other minor factors (like Factor XIII) not yet assayed in these experiments. What may be important is what the citrated cryoprecipitate does not contain.

As was mentioned above, it has been found that addition of citrate to frozen plasma during the unfreezing process appears to be almost as effective at increasing the amount of cryoprecipitate as adding the citrate prior to freezing. Of course, in most cases it is more convenient to add the citrate to the blood bags prior to collection or expressing the plasma, or perhaps during the pooling of plasma prior to freezing. However, there are cases where pooled plasma is stored and shipped in the frozen state so that it is a significant advantage that the new enhanced citrate process can be used with such plasma even if the plasma was frozen before the new process was even invented. However, for best results the added citrate must be present during the thawing process. Increasing the citrate concentration after thawing is not nearly as effective.

In investigating this phenomenon it was discovered that freezing is not even necessary. In one experiment five 40 ml aliquots of human plasma were brought to 10% wt/v trisodium citrate by the addition of 10 ml aliquots of a 50% wt/v trisodium citrate stock solution. After mixing the aliquots were stored for 24 hours at 4° C. At the end of this time a large white precipitate had formed in each sample. The samples were centrifuged at 1.500×g for 10 minutes in a refrigerated centrifuge to pellet the precipitate. The supernatant was carefully poured off, and each pellet was redissolved in 10 ml of 0.9% NaCl. A check of pH showed that it remained in the normal physiological range. Calcium chloride was added to the solutions to overcome the citrate (that is, to substitute for the calcium sequestered by the citrate so that clotting assays could proceed normally), and each solution was sent to an independent laboratory for determination of Factor VIII and fibrinogen. The results are shown in the following Table

| Aliquot | Pellet | | Supernatant | |
|---|---|---|---|---|
| 4° C. | Factor VIII | Fibrinogen | Factor VIII | Fibrinogen |
| 1 | 422% | 1,205 mg/dl | not detected | not detected |
| 2 | 408% | 1,100 mg/dl | not detected | not detected |
| 3 | 436% | 1,010 mg/dl | not detected | not detected |
| 4 | 389% | 1,196 mg/dl | not detected | not detected |
| 5 | 401% | 1,301 mg/dl | not detected | not detected |

These results show that essentially all of the Fibrinogen and Factor VIII ended up in the pellet. Since the pellet from 40 ml of plasma was resuspended in 10 ml of saline one would expect a four-fold increase if all of these proteins were in the pellet. This is essentially what the tests show within their margin of error. Similarly, the Fibrinogen readings are about four times higher than normal. The small amount of Factor VIII and Fibrinogen remaining in the supernatant is below the detection limits of the tests. This finding shows that it is possible to dispense with the cumbersome freezing and thawing steps altogether. With this method "cryo" takes on it's preferred etymological meaning of "icy cold" rather than frozen.

In fact, it appears that even icy cold is not strictly necessary. The following table shows the results of an experiment carried out exactly like the previous experiment except that the aliquots were allowed to rest for 24 hours at room temperature (approximately 21° C.) prior to centrifugation. The results show that the separation was almost as good as at the lower temperature. Further experimentation is necessary to determine whether 4° C. is a "magic value" or if some temperature lower than 21° C. but higher than 4° C. will produce optimum results. Also, it is possible that a longer time at 21° C. will produce improved results. In any case, the difference between the results at 21° C. and 4° C. is small. Either of these temperatures with citrate produces yields superior to current frozen cryoprecipitates without additional citrate. It would appear that simple incubation with elevated levels of citrate allows binding of the citrate or "citrification" of the proteins which results in precipitation. When the citrate level is reduced (as in resuspension in saline) the proteins readily go back into solution—indicating that they are not damaged by the "citrifying" process.

| Aliquot | Pellet | | Supernatant | |
|---|---|---|---|---|
| 21° C. | Factor VIII | Fibrinogen | Factor VIII | Fibrinogen |
| 1 | 386% | 1,100 mg/dl | not detected | not detected |
| 2 | 411% | 992 mg/dl | not detected | not detected |

The enhanced production of cryoprecipitate according to the present invention opens up the possibility of readily preparing a clotting factor concentrate from single donors or small pools of donors without any freezing step and without using chromatography. Because the amount of clotting factor recoverable from a single unit of blood is generally large enough only for pediatric treatment, it is usually necessary or desirable to pool the plasma from a small, defined pool of donors (usually fewer than ten donors). By using a small and consistent donor pool, the possibility of blood-borne infection can be significantly decreased.

To produce optimal single or limited donor pool clotting factor plasma is first collected to contain an optimal concentration of trisodium citrate. The optimum concentration is between 10% and 15% wt/vol. with about 12% wt/vol. being a preferred concentration in many cases. One means of collecting the plasma is to centrifuge freshly collected units of whole blood in a blood bag centrifuge as is well known to those of skill in the art. At that point the supernatant plasma can be expressed into a separate blood bag containing sufficient stock citrate solution (e.g., 50% wt/vol. trisodium citrate at pH 7.0 is convenient) to bring the final citrate concentration to the desired level. If a pool is to be made, several units of plasma can be expressed into a single large blood bag. Other means of achieving the same end will be apparent to those of ordinary skill in the art. For example, plasma collected by plasmapheresis can be collected directly into blood bags containing the extra citrate or the extra citrate can be added following collection.

The preferred method is to store the citrated plasma in the cold (4-7° C.) for 24 hours. During this time a heavy cryoprecipitate will form; after the cryoprecipitate has completely formed, it is separated from the supernatant plasma. Again, centrifugation of the blood bag is a good method of achieving this separation of cryoprecipitate and supernatant plasma although filtration of other methods may be used. Although cold precipitation is the preferred method, the plasma may also be frozen and the precipitation stage performed following thawing. The least preferred method is to freeze without added citrate and to add the citrate stock solution to the frozen plasma prior to thawing.

The resulting cryoprecipitate or the components thereof can advantageously be used to treat congenital as well as "acquired" deficiencies. Fore example, the material is useful in the treatment of hemophilia, liver disease, transplant cases and sepsis.

As explained above, the clotting factors are essentially all present in the cryoprecipitate which can be redissolved in water or saline. However, merely redissolving the cryoprecipitate will produce a solution that is primarily fibrinogen. If sufficient amounts of this solution were administered to a patient to provide normal levels of clotting factors, the patient would receive a tremendous excess of protein mostly in the form of fibrinogen. Therefore, some method must be used to decrease the amount of fibrinogen relative to the Factor VIII. It is known in the art that extracting the cryoprecipitate with cold saline preferentially dissolves the clotting factors while leaving most of the cryoprecipitate (fibrinogen and fibronectin) as a solid. For example, in one experiment cryoprecipitate was produced according to the above method using 12% wt./vol. trisodium citrate. Equal amounts of cryoprecipitate were resuspended for 30 minutes at 9-10° C. in a volume of cold buffer equal to the volume of cryoprecipitate. A typical unit of blood (approximately 250 ml) yields around 20 ml of cryoprecipitate. The average value of Factor VIII in the starting blood is 1 unit/ml so that the cryoprecipitate should contain between 200 and 300 units of Factor VIII activity.

Either cold 0.9% saline pH 7.0 or cold 0.3M calcium chloride in 0.9% saline pH7.0 was used as buffer for the extraction. Following the extraction in the cold (i.e., below about 10° C.), the material was recentrifuged to pellet the undissolved material. The supernatants were assayed, and it was discovered that the saline extract contained 4.1 units/ml of Factor VIII while the calcium saline extract contained 4.3 units/ml of Factor VIII. These are essentially equivalent amounts due to the level of precision of the assay. Further, the amounts of Factor VIII extracted were nearly 100% of that available. The most striking difference is seen when the amount of fibrinogen in the extract is measured. It is believed that the addition of calcium ions prevents the dissolution of fibrinogen. Depending on the experiment the amount of fibrinogen in the calcium extraction varied from one half to less than one fifth as much fibrinogen (generally in the range of 100 mg/dl) as compared to traditional extraction methods. This level of fibrinogen is sufficiently low as to be almost negligible in terms of therapeutic administration. Lowering the pH of the extraction medium to pH 5.5 may slightly lower the amount of Factor VIII extracted but further reduces the level of fibrinogen to essentially zero. Thus, it is possible to readily produce a Factor VIII solution with levels of fibrinogen that are not significant when the solution is used to treat a patient.

Table I gives a clearer picture of the purification attained by the present invention. The table shows amounts of protein in mg and is adjusted so that each starting fraction (e.g., cryoprecipitate) contains 100 units of Factor VIII activity. AHF stands for anti-hemophilia factor, a semi-purified Factor VIII concentrate. IP indicates intermediate purity while HP indicates high purity. Note that traditional cryoprecipitate shows an apparent higher activity of Factor VIII. This is because the citrated cryoprecipitate of the present invention has relatively more fibrinogen than traditional cryoprecipitate (that is, more total protein that is not Factor VIII). As shown above when expressed on overall recovery of Factor VIII, citrated cryoprecipitate contains essentially all of the Factor VIII present in the original plasma whereas traditional cryoprecipitate does not. The other proteins present in the citrated cryoprecipitate (albumin and α, β, and γ globulins) are present primarily as trapped inclusions and are present in essentially the same proportions as in traditional cryoprecipitate. The improvements in purity when going from cryoprecipitate to IP-AHF to HP-AHF are occasioned by the removal of fibrinogen, albumin and globulins. It can be seen that the saline extract of citrated cryoprecipitate is nearly as pure as IP-AHF on a total protein basis. The inventive calcium extract is considerably better than IP-AHF but not as good as HP-AHP on a total protein basis. Low pH calcium extraction, not shown in the table, yields a product even lower in total protein having essentially no fibrinogen. Thus, when combined with citrated cryoprecipitate, the inventive extraction method allows simple production of a pure AHP concentrate from single donors or limited donor pools.

TABLE I (Values expressed as mg of protein giving 100 units of Facto VIII activity)

|  | Fibrinogen | Albumin | α | β | γ | Total Protein |
| --- | --- | --- | --- | --- | --- | --- |
| Plasma | 1,700 | 32,000 | 6,500 | 6,000 | 7,000 | 53,200 |
| Cryoppt | 320 | 350 | 85 | 68 | 77 | 900 |
| IP-AHF | 120 | 35 | 0 | 35 | 10 | 200 |
| HP-AHF | 32 | 0 | 0 | 25 | 3 | 60 |
| Citrate-Cryo | 887 | 380 | 92 | 73 | 85 | 1517 |
| Saline Extract | 81 | 73 | 0 | 47 | 26 | 227 |
| Calcium Extract | 35 | 56 | 0 | 34 | 14 | 139 |

The inventive method of AHF production as diagrammed in FIG. 1 consists of first producing citrated cryoprecipitate. Preferably this is prepared from single donor plasma or from plasma pools produced from a limited number of donors. Ideally, the required concentration of citrate (10-15% wt./vol. trisodium citrate) is added as soon as practicable after plasma collection. Preferably, the citrated cryoprecipitate is collected after holding the plasma at about 4-6° C. for about 24 hours without freezing. It is also possible to freeze the plasma if it is not convenient to immediately effect separation of the citrated cryoprecipitate. In that case, the plasma is later thawed and held in the cold to allow complete formation of the cryoprecipitate. The cryoprecipitate is them separated from the supernatant by centrifugation or filtration. The supernatant plasma can be used for further fractionation or as a blood volume expander. The citrated cryoprecipitate is then extracted with the calcium saline extraction medium. This yields an AHP concentrate that can be used immediately in therapy. If desired calcium and or citrate can be removed from the concentrate using chromatographic and ultrafiltration methods well known to those of skill in the art. Thus the present invention makes is possible for a blood bank to provide high quality AHP using simple equipment and procedures.

The undissolved material following low temperature calcium extraction is primarily fibrinogen (and fibronectin). Partly because of the added calcium it is possible to cause this material to gel if the temperature is raised to about 50° C. for about five minutes. At a lower temperature (i.e., room temperature) the material will eventually gel but heating above room temperature greatly accelerates the process. Most likely this is a clotting phenomenon mediated by one of the alternative coagulation pathways and potentiated by the added calcium ions. In one experiment the supernatant (containing the concentrated clotting factors) was removed and the fibrinogen pellet rinsed with cold buffer prior to the heating. In a second experiment the fibrinogen was heated without carefully removing the supernatant. In either case the material gelled forming a transparent semisolid which became increasingly opalescent and tough over the ensuing 12 hours. However, after 24 or so hours the material from the second experiment began to liquefy suggesting that the supernatant had contributed plasminogen which digested the fibrin.

This provides a simple method for preparing fibrin/fibrinogen membrane or fabric. After the clotting factor concentrate is withdrawn (e.g., in a sterile blood bag), it is possible to rinse the fibrinogen precipitate as necessary and mold it into a thin sheet all without opening the bag and compromising sterility. Once the fibrinogen has been properly molded, the bag is heated to form the fibrin/fibrinogen fabric. Depending on the desired strength of the material, it can be allowed to "harden" for eight or so hours prior to use.

The fibrin/fibrinogen material can also be reinforced by embedding a mesh in the thin sheet. Because one of the advantages of the fibrin material is that it is ultimately absorbed by the body, it is advantageous to make any reinforcing mesh from a biodegradable or absorbable material such as those commonly used to produce absorbable suture material. While the preferred method is ideal for use by hospitals to prepare fibrin fabric immediately prior to surgery (possibly using autologous blood), it is also possible to lyophilize the fibrin fabric so that it can be produced in advance and at remote locations.

The invention covers the process and products obtained by the process. The following claims are thus to be understood to include what is specifically illustrated and described above, what can be obviously substituted and also what incorporates the essential idea of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A method for producing a clotting factor concentrate without using chromatography comprising the steps of:
   adding trisodium citrate to plasma to yield a concentration of trisodium citrate of between about 10% weight by volume and about 15% weight by volume;
   allowing cryoprecipitate to form in the plasma;
   separating the cryoprecipitate from the plasma;
   extracting in the cold, below 10 C. the cryoprecipitate with an extraction solution containing calcium chloride; and
   separating the cryoprecipitate from the extraction solution wherein the separated extraction solution is the clotting factor concentrate.

2. The method according to claim 1, wherein forming cryoprecipitate does not involve freezing the plasma.

3. The method according to claim 1, wherein the step of separating the cryoprecipitate from the plasma employs centrifugation.

4. The method according claim 1 further comprising the step of removing citrate from the clotting factor concentrate.

5. The method according claim 1 further comprising the step of removing calcium from the clotting factor concentrate.

6. The method according to claim 1, wherein the step of separating the cryoprecipitate from the extraction solution employs centrifugation.

7. The method according to claim 1, wherein the extraction solution contains about 0.9% sodium chloride, weight by volume and about 0.3M calcium chloride.

8. The method according to claim 1, wherein the extraction solution has a pH between about 5.0 and about 7.0.

9. The method according to claim 1, wherein the step of adding trisodium citrate is accomplished by collecting the plasma directly into a container holding the trisodium citrate.

10. A method for producing a clotting factor concentrate without using chromatography comprising the steps of:
    adding trisodium citrate to plasma to yield a concentration of trisodium citrate of about 12% weight by volume;
    allowing cryoprecipitate to form in the plasma;
    separating the cryoprecipitate from the plasma by centrifugation;
    extracting in the cold, below 10 C. the cryoprecipitate with an extraction solution comprising a cold solution containing sodium chloride and calcium chloride; and
    separating the cryoprecipitate from the extraction solution by centrifugation wherein the separated extraction solution is the clotting factor concentrate.

11. The method according to claim 10, wherein forming cryoprecipitate does not involve freezing the plasma.

12. The method according claim 10 further comprising the step of removing citrate from the clotting factor concentrate.

13. The method according claim 10 further comprising the step of removing calcium from the clotting factor concentrate.

14. The method according to claim 10, wherein the extraction solution contains about 0.9% sodium chloride, weight by volume and about 0.3M calcium chloride.

15. The method according to claim 10, wherein the extraction solution has a pH between about 5.0 and about 7.0.

16. The method according to claim 10, wherein the extraction solution has a pH of about 5.5.

17. The method according to claim 10, wherein the step of adding trisodium citrate is accomplished by collecting the plasma directly into a container holding the trisodium citrate.

* * * * *